United States Patent
Park et al.

(10) Patent No.: US 12,089,929 B2
(45) Date of Patent: Sep. 17, 2024

(54) WEARABLE PHOTOLUMINESCENCE SENSOR AND REMOTE SENSING APPARATUS COMPRISING SAME

(71) Applicant: LG Display Co., Ltd., Seoul (KR)

(72) Inventors: Jin-Woo Park, Paju-si (KR); Changjin Lim, Paju-si (KR); Soyeon Lee, Paju-si (KR); Su Seok Choi, Paju-si (KR); Kiseok Chang, Paju-si (KR); Jeong Min Moon, Paju-si (KR); Soon Shin Jung, Paju-si (KR); Sungpil Ryu, Paju-si (KR); Jihwan Jung, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 842 days.

(21) Appl. No.: 17/270,815

(22) PCT Filed: Aug. 23, 2019

(86) PCT No.: PCT/KR2019/010780
§ 371 (c)(1),
(2) Date: Feb. 23, 2021

(87) PCT Pub. No.: WO2020/040606
PCT Pub. Date: Feb. 27, 2020

(65) Prior Publication Data
US 2021/0275062 A1    Sep. 9, 2021

(30) Foreign Application Priority Data

Aug. 23, 2018   (KR) .................. 10-2018-0098469

(51) Int. Cl.
*A61B 5/1455*   (2006.01)
*A61B 5/00*     (2006.01)

(52) U.S. Cl.
CPC .......... *A61B 5/1455* (2013.01); *A61B 5/6801* (2013.01)

(58) Field of Classification Search
CPC ............. A61B 5/1455; A61B 5/14551; A61B 5/14552; A61B 5/14556; A61B 5/0059;
(Continued)

(56) References Cited

U.S. PATENT DOCUMENTS 10,159,434 B1 * 12/2018 Alla ................... G01N 21/6428
2014/0171762 A1   6/2014 LeBoeuf et al.
(Continued)

FOREIGN PATENT DOCUMENTS

KR   10-2012-0003043 A    1/2012
KR      20160017601 A *   5/2015
(Continued)

OTHER PUBLICATIONS

Rui Liu, et al.Multiple approaches for enhancing all-organic electronics photoluminescent sensors: Simultaneous oxygen and pH monitoring, Analytica Chimica Acta 779 (2013) 70-78, Elsevier, journal homepage: www.elsevier.com/locate/aca in 9 pages.
(Continued)

*Primary Examiner* — Yi-Shan Yang
*Assistant Examiner* — Kyle W. Kretzer
(74) *Attorney, Agent, or Firm* — POLSINELLI PC (57) ABSTRACT

A wearable photoluminescence sensor, which is portable and has improved sensitivity and accuracy, and a remote sensing apparatus comprising same, the disclosed wearable photoluminescence sensor includes a reflective support and a semi-permeable filter disposed over and under translucent photodiodes, thus allows light of a second wavelength band, having the photoluminescence properties of getting lost or
(Continued)

passing through, to be reflected again and thus maximally utilized, and thereby allows sensitivity and accuracy to be improved.

15 Claims, 6 Drawing Sheets

(58) Field of Classification Search
CPC ... A61B 5/0071; A61B 5/0075; A61B 5/0082; A61B 5/6801; A61B 2562/0233
See application file for complete search history.

(56) References Cited

U.S. PATENT DOCUMENTS

| | | | |
|---|---|---|---|
| 2017/0181635 A1* | 6/2017 | Liu | A61B 5/02433 |
| 2019/0150811 A1* | 5/2019 | Evans | A61M 5/172 |
| 2019/0378880 A1* | 12/2019 | Zalar | H10K 77/111 |

FOREIGN PATENT DOCUMENTS

| | | |
|---|---|---|
| KR | 10-2016-0017601 A | 2/2016 |
| KR | 10-2017-0136249 A | 12/2017 |
| WO | WO 2018/131638 A1 | 7/2018 |

OTHER PUBLICATIONS

Korean Office Action dated Apr. 28, 2023 issued in Patent Application No. 10-2018-0098469 w/English Translation (12 pages).

* cited by examiner

WEARABLE PHOTOLUMINESCENCE SENSOR AND REMOTE SENSING APPARATUS COMPRISING SAME

CROSS-REFERENCE TO RELATED APPLICATION

This application is a National Phase Entry of PCT International Application No. PCT/KR2019/010780 filed on Aug. 23, 2019, which claims priority to Korean Application No. 10-2018-0098469 filed on Aug. 23, 2018, which are hereby incorporated by reference in their entirety.

BACKGROUND

Field of the Disclosure

The present disclosure relates to a wearable photoluminescence sensor which is portable and has improved sensitivity and accuracy, and to a remote sensing device having the same.

Description of the Background

A photoluminescence sensor refers to a sensor in which a photo-luminescence characteristic of a sensing film varies based on a specific compound or element adsorbed into the sensing film.

The photoluminescence sensor includes a sensor film, a light-emitting element and a photo-diode. The photoluminescence sensor has a very simple operation principle, has higher operational reliability and senses a wide range of compounds. The photoluminescence sensor is used in a wide variety of fields such as environment, medical, food, security, and chemical engineering industries.

In recent years, as demand for portable and miniaturized sensors has increased, need for an alternative light-emitting element to a laser and a LED that have been used as a conventional light-emitting element has increased. Therefore, an organic electroluminescence element is attracting attention as the alternative light-emitting element in that the organic electroluminescence element may integrate with the photoluminescence sensor in an easier manner than the conventional light-emitting element may, and may have a lower manufacturing cost and thus may be applied to a disposable sensor and may be thin and light and thus may be applied to a portable sensor.

Currently, in a field of the photoluminescence sensor based on the organic electroluminescence element, research on increasing or controlling an operating time of the electroluminescence element and an intensity of light therefrom in order to increase an intensity of photo-luminescence emitted from the sensing film, and development related to easy integration between the organic electroluminescence element and the photoluminescence sensor are in progress.

A wearable photoluminescence sensor is a generic term of a device that is attached directly to a human skin and senses a specific chemical element or a mechanical movement. Recently, as micro sensing and diagnostic medicine real related techniques have developed, interest in the wearable photoluminescence sensor is increasing.

Accordingly, studies on the wearable photoluminescence sensor that may be carried or worn while being able to measure amounts of moisture, oxygen, active oxygen, and serum in the human skin in real time are actively being conducted.

SUMMARY

Accordingly, the present disclosure is to provide a wearable photoluminescence sensor which is portable and has improved sensitivity and accuracy, and provide a remote sensing device having the same.

To this end, in the wearable photoluminescence sensor according to the present disclosure, a transflective filter is disposed between a light-emitting element and a translucent photo-diode, and a reflective support is disposed on the translucent photo-diode.

Accordingly, the wearable photoluminescence sensor according to the present disclosure has the translucent photo-diode and has a structure in which the light-emitting element and the translucent photo-diode constitute different layers, respectively and at least partially and vertically non-overlap each other, such that the translucent photo-diode may absorb light on both opposite faces thereof.

As a result, in the wearable photoluminescence sensor according to the present disclosure, the translucent photo-diode may absorb light on both opposite faces thereof, such that sensitivity of the sensor may be further improved.

Further, in the wearable photoluminescence sensor according to the present disclosure, a reflective support and a transflective filter are respectively disposed above and below the translucent photo-diode. Accordingly, in the wearable photoluminescence sensor according to the present disclosure, light of a second wavelength band having a photo-luminescence characteristic that has otherwise been lost or transmitted may be re-reflected and thus may be utilized to a maximum degree, so that sensitivity and accuracy of the wearable photoluminescence sensor may be improved.

A wearable photoluminescence sensor according to an aspect of the present disclosure includes: a sensing film: a light-emitting element disposed on the sensing film: a translucent photo-diode disposed above the light-emitting element and spaced therefrom and at least partially and vertically non-overlapping the light-emitting element: a transflective filter disposed between the light-emitting element and the translucent photo-diode: and a reflective support disposed above the translucent photo-diode and spaced therefrom.

As described above, the wearable photoluminescence sensor according to the present disclosure has the translucent photo-diode, and has a structure in which the transflective filter is disposed between the light-emitting element and the translucent photo-diode, and the reflective support is disposed above the translucent photo-diode, such that the translucent photo-diode may absorb light on both opposite faces thereof.

As a result, in the wearable photoluminescence sensor according to the present disclosure, the translucent photo-diode may absorb light on both opposite faces thereof, thereby achieving a larger amount of excitation of the sensing film.

In particular, the transflective filter according to the aspect of the present disclosure may selectively reflect light of a first wavelength band as emitted from the light-emitting element to minimize an interference effect due to noises otherwise flowing into the translucent photo-diode, and may selectively allow light of a second wavelength band generated from the sensing film to transmit therethrough.

As a result, the wearable photoluminescence sensor according to the aspect of the present disclosure may minimize loss of light of the second wavelength band having the photo-luminescence characteristic as emitted from the sensing film and flowing into the translucent photo-diode, such that sensing accuracy and sensitivity may be improved.

Further, a wearable remote sensing device according to an aspect of the present disclosure includes a sensor attached to a living body to measure a biological state thereof: a transmitter for wirelessly transmitting the biological state measured by the sensor to a remote location: a receiver for wirelessly receiving an alarm from the remote location: a power supply for supplying power to each of the sensor, the transmitter and the receiver: a controller configured to transmit information measured by the sensor to the transmitter, and to inform a user of the alarm received by the receiver and information about a power amount of the power supply.

In this connection, the sensor may include a sensing film: a light-emitting element disposed on the sensing film: a translucent photo-diode disposed above the light-emitting element and spaced therefrom and at least partially and vertically non-overlapping the light-emitting element: a transflective filter disposed between the light-emitting element and the translucent photo-diode: and a reflective support disposed above the translucent photo-diode and spaced therefrom.

Accordingly, the wearable remote sensing device according to the present disclosure uses the sensor to detect the biological state of the user in real time, and wirelessly transmits the biological state to the remote location such as a medical facility, such that a medical staff may easily check a health status of the user.

As a result, the wearable remote sensing device according to the aspect of the present disclosure may detect the biological condition of the user in real time and easily check the health status of the user, such that a medical staff at the remote location may perform early diagnosis of diseases.

The wearable photoluminescence sensor according to the present disclosure has the translucent photo-diode, and has a structure in which the transflective filter is disposed between the light-emitting element and the translucent photo-diode, and the reflective support is disposed above the translucent photo-diode, such that the translucent photo-diode may absorb light on both opposite faces thereof.

As a result, in the wearable photoluminescence sensor according to the present disclosure, the translucent photo-diode may absorb light on both opposite faces thereof, such that sensitivity of the sensor may be further improved.

Further, in the wearable photoluminescence sensor according to the present disclosure, the reflective support and the transflective filter are respectively disposed above and below the translucent photo-diode. Accordingly, in the wearable photoluminescence sensor according to the present disclosure, light of the second wavelength band having a photo-luminescence characteristic that has otherwise been lost or transmitted may be re-reflected. Thus, the light of the second wavelength band may be utilized to a maximum degree, so that sensitivity and accuracy of the wearable photoluminescence sensor may be improved.

Further, in the wearable photoluminescence sensor according to the present disclosure, the reflective support and the transflective filter are respectively disposed above and below the translucent photo-diode. Accordingly, in the wearable photoluminescence sensor according to the present disclosure, light of the second wavelength band having a photo-luminescence characteristic that has otherwise been lost or transmitted may be re-reflected and thus may be re-used, so that sensitivity and accuracy of the wearable photoluminescence sensor may be improved.

As a result, the wearable photoluminescence sensor according to the aspect of the present disclosure may minimize loss of light of the second wavelength band having the photo-luminescence characteristic as emitted from the sensing film and flowing into the translucent photo-diode, such that sensing accuracy and sensitivity may be improved.

BRIEF DESCRIPTION OF THE DRAWINGS

The accompanying drawings, which are included to provide a further understanding of the disclosure and are incorporated in and constitute a part of the present disclosure, illustrate aspects and together with the description serve to explain the principles of the disclosure.

In the drawings.

DETAILED DESCRIPTIONS

The above features and advantages will be described in detail later with reference to the accompanying drawings. Accordingly, a person with ordinary knowledge in the technical field to which the present disclosure belongs will be able to easily implement the technical idea of the present disclosure. In describing the present disclosure, when it is determined that a detailed description of a known component related to the present disclosure may unnecessarily obscure gist the present disclosure, the detailed description is omitted. Hereinafter, various aspects according to the present disclosure will be described in detail with reference to the accompanying drawings. In the drawings, the same reference numerals are used to indicate the same or similar elements.

Hereinafter, a wearable photoluminescence sensor according to the various aspects of the present disclosure and a remote sensing device having the same will be described in detail with reference to the accompanying drawings.

Figure 1:
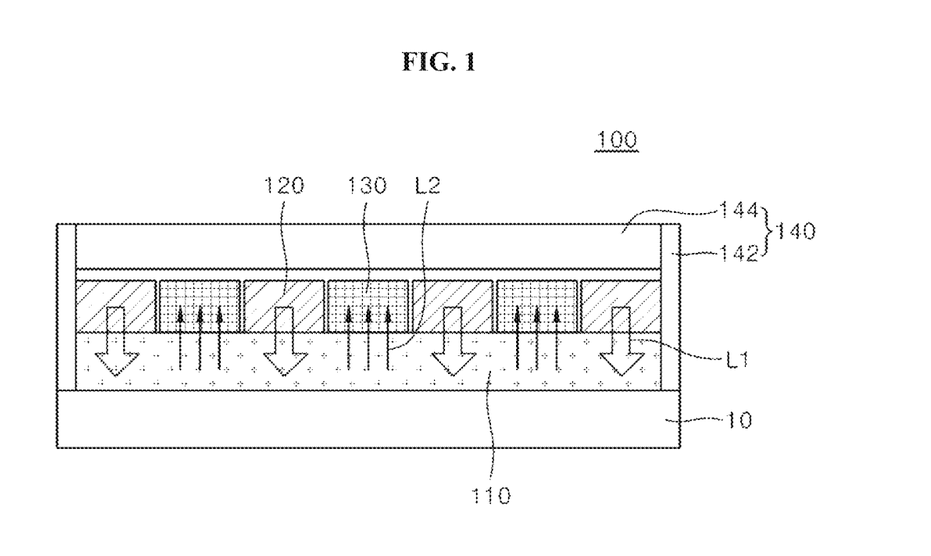
FIG. 1 is a combined cross-sectional view showing a wearable photoluminescence sensor according to a first aspect of the present disclosure.

FIG. 1 is a combined cross-sectional view showing a wearable photoluminescence sensor according to a first aspect of the present disclosure.

Referring to FIG. 1, a wearable photoluminescence sensor 100 according to the first aspect of the present disclosure may include a sensing film 110, a light-emitting element 120, a photo-diode 130, and a support 140.

The sensing film 110 is attached to a living body as a sensing target. For example, the sensing target may be a user. The sensing film 110 may be made of a material capable of sensing oxygen, moisture, nitric oxide, serum, and the like. To this end, the sensing film 110 may contain at least one material selected from a rhodamine-based organic coloring agent including rhodamine 6G, rhodamine 110, rhodamine 700, sulforhodamine B, and sulforhodamine 101, and umbelliferone.

The light-emitting element 120 is disposed on the sensing film 110. The light-emitting element 120 may emit light of a specific wavelength among red, green, and blue wavelength bands. However, the disclosure is not limited thereto. Light of the specific wavelength may be light of specific wavelength bands among infrared, ultraviolet, and visible wavelength bands. In this connection, the light-emitting element 120 may be an LED (light-emitting diode) or an organic electroluminescence element. The organic electroluminescence element may be referred to as an organic light-emitting diode. Use of the organic electroluminescence element having flexible characteristics may allow the sensor 100 to be easily attached to the living body as a sensing target.

In this connection, the sensing film 110 absorbs light L1 emitted from the light-emitting element 120. Further, the sensing film 110 adsorbs a specific compound or element such as oxygen or active oxygen, moisture, nitric oxide, serum, etc. as an analyte as produced from the skin.

In this connection, the sensing film 110 may absorb light L1 irradiated from the light-emitting element 120, and then may emit light L2 of a specific wavelength having photoluminescence PL characteristic varying based on a type of the specific compound or element toward the photo-diode 130.

The photo-diode 130 is disposed on the sensing film 110. The photo-diodes 130 and the light-emitting elements 12 may be arranged alternately with each other and spaced apart from each other. The photo-diode 130 detects light L2 emitted from the sensing film 110, and measures an amount of light including information about a content of oxygen ($O_2$) or active oxygen, moisture, nitric oxide, or serum and generates photocurrent based on the measured amount. To this end, means for analyzing and calculating the light L2 emitted from the sensing film 110 may be further provided in the sensor 100.

The support 140 covers a top face of the sensing film 110 and side faces of the light-emitting element 120. The support 140 includes a vertical portion 142 attached to a top face of the sensing film 110 and side faces of the light-emitting element 120, and a horizontal portion 144 extending horizontally from the vertical portion 142 and covering top faces of the light-emitting element 120 and the photo-diode 130. However, in the aspects of the present disclosure, a shape of the support 140 is not limited thereto. A structure of the support 140 may vary in a manner obvious to a person skilled in the art.

The wearable photoluminescence sensor 100 according to the first aspect of the present disclosure as described above includes the sensing film 110, the light-emitting element 120, and the photo-diode 130 that measures an intensity of light emitted from the sensing film 110.

In this connection, a light intensity characteristic of photoluminescence PL emitted from the sensing film 110 may vary based on a type of the analyte adsorbed into the sensing film 110. Thus, the wearable photoluminescence sensor 100 according to the first aspect of the present disclosure may measure the type and a concentration of the analyte, based on the variation in the light intensity characteristic of photoluminescence PL. That is, the light-intensity characteristic of the photoluminescence PL emitted from the sensing film 110 varies based on the type and/or the concentration of the analyte adsorbed into the sensing film 110. Further, the wearable photoluminescence sensor 100 detects the light intensity of photo-luminescence PL and may measure the concentration of the analyte, based on the intensity.

This principle will be described in more detail below with reference to the accompanying drawings.

Figure 2:
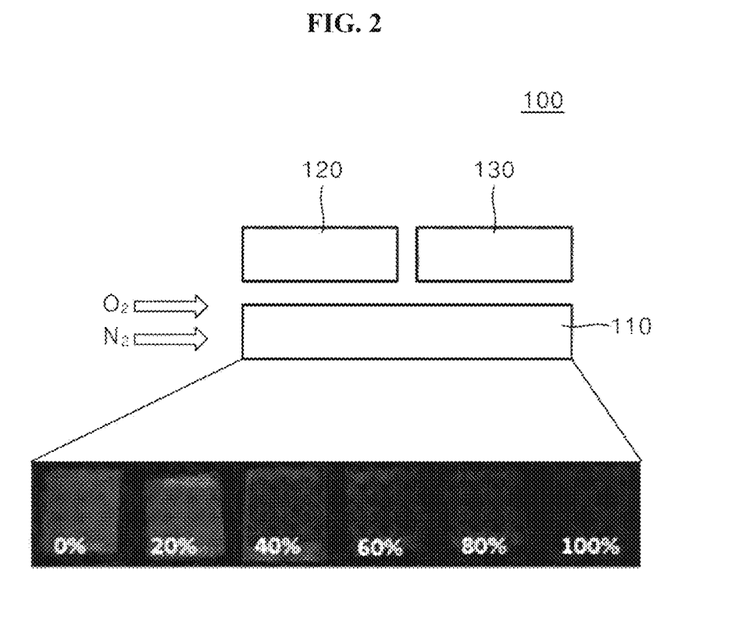
FIG. 2 is a schematic diagram for describing an operating principle of the wearable photoluminescence sensor according to the first aspect of the present disclosure.
Figure 3:
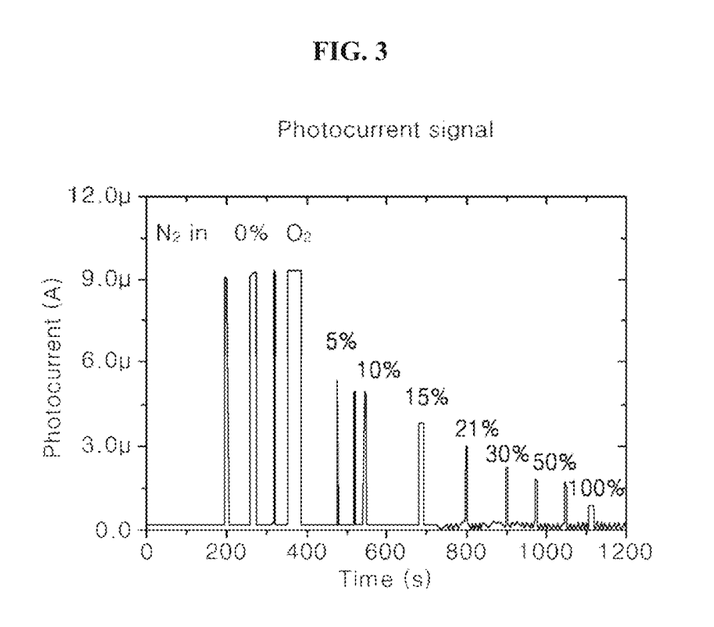
FIG. 3 is a graph for describing a photocurrent generation principle.
Figure 4:
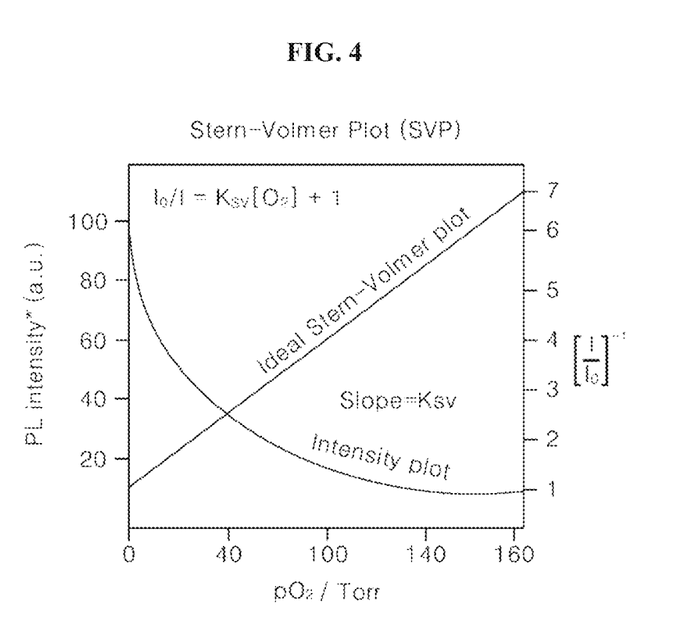
FIG. 4 is a graph for describing a Stern Volmer plot.

FIG. 2 is a schematic diagram for describing the operating principle of the wearable photoluminescence sensor according to the first aspect of the present disclosure. Further, FIG. 3 is a graph for describing a principle of photocurrent generation. FIG. 4 is a graph for describing the Stern Volmer plot.

First, as shown in FIG. 2 and FIG. 3, in an example, when light of the first wavelength band of 550 nm from the light-emitting element 120 is irradiated to the sensing film 110, the sensing film 110 absorbs light of the first wavelength band, and then emits light of the second wavelength band of 650 nm which becomes larger than the first wavelength band due to the photoluminescence. In this connection, when a concentration of oxygen varies, the light intensity of the photoluminescence changes as quenching proceeds. The photo-diode 130 may absorb the light of the second wavelength band into which the light of the second wavelength band converts and may generate a photocurrent signal based on the absorbed light. The wearable photoluminescence sensor 100 according to the first aspect of the present disclosure may include an oxygen supply device capable of adjusting an oxygen concentration or may be connected to the oxygen supply device.

As shown in FIG. 4, it may be identified that the photocurrent signal changes based on the concentration of the supplied oxygen. In this connection, a ratio between the photocurrent $I_0$ under absence of oxygen and the photocurrent I under presence of oxygen may be calculated and a linear Stern-Volmer plot may be created based on the ratio. In this connection, a $K_{sv}$ value indicates a slope, which means the sensitivity.

Referring back to FIG. 1, the light intensity characteristic of photoluminescence PL emitted from the sensing film 110 may vary based on a type and/or a concentration of the analyte adsorbed into the sensing film 110. Thus, the wearable photoluminescence sensor 100 according to the first aspect of the present disclosure may measure the type and the concentration of the analyte, based on the variation in the light intensity characteristic of photoluminescence PL.

As a result, in the wearable photoluminescence sensor 100 according to the first aspect of the present disclosure, the sensing film 110, the light-emitting element 120, and the photo-diode 130 are integrated with each other. Thus, a structure of the sensor 100 is simple, and the manufacturing cost thereof is low. Further, the light-emitting element 120 and the photo-diode 130 constitute the same layer, such that a thickness of the wearable photoluminescence sensor 100 decreases and thus the sensor 100 is slim.

That is, in the wearable photoluminescence sensor 100 according to the first aspect of the present disclosure, the light-emitting elements 120 and the photo-diodes 130 constitute the same layer on the sensing film 110 and are arranged alternately with each other and are spaced apart from each other by a regular spacing.

Accordingly, the wearable photoluminescence sensor 100 according to the first aspect of the present disclosure has flexibility and elasticity such that the sensor 100 may be deformed in a conformal manner to a curvature and an area of a surface to which the sensor 100 is attached, so that the sensor 100 may be attached to and detached from the user. Further, the light intensity characteristic of photoluminescence PL emitted from the sensing film 110 may vary based on a type and/or a concentration of the analyte adsorbed into the sensing film 110. Thus, the wearable photoluminescence sensor 100 according to the first aspect of the present disclosure may measure the type and the concentration of the analyte, based on the variation in the light intensity characteristic of photoluminescence PL.

Accordingly, the wearable photoluminescence sensor 100 according to the first aspect of the present disclosure may detect a photocurrent corresponding to an oxygen concentration.

Hereinafter, various aspects of the wearable photoluminescence sensor capable of further improving biological detection accuracy will be described below.

The wearable photoluminescence sensor according to a second aspect of the present disclosure has a translucent photo-diode and has a structure in which the light-emitting element and the translucent photo-diode constitute different layers, respectively and at least partially and vertically non-overlap each other, such that the translucent photo-diode may absorb light on both opposite faces thereof.

To this end, in the wearable photoluminescence sensor according to the second aspect of the present disclosure, a transflective filter is disposed between the light-emitting element and the translucent photo-diode, and a reflective support is disposed over the translucent photo-diode. As a result, the translucent photo-diode may absorb light on both opposite faces thereof. Thus, even when the light-emitting element of the wearable photoluminescence sensor according to the second aspect of the present disclosure is activated using the same power level as that used in the first aspect, the wearable photoluminescence sensor according to the second aspect of the present disclosure may detect the light of the second wavelength band in a more reliable manner than in the first aspect. Thus, the sensitivity of the wearable photoluminescence sensor according to the second aspect of the present disclosure may be further improved.

In the wearable photoluminescence sensor according to the first aspect of the present disclosure as described above, when light of the first wavelength band is emitted from the light-emitting element to excite the sensing film, not an entirety of the light emitted from the light-emitting element may be absorbed into the sensing film, but a portion thereof may be absorbed into the photo-diode. Therefore, when interference in which the light of the first wavelength band emitted from the light-emitting element other than the light of the second wavelength band together with the light of the second wavelength band is incident into the photo-diode occurs, the photocurrent signal of the sensing film based on the oxygen concentration may have noise due to crosstalk. That is, the light of the second wavelength band and the light of the first wavelength band are incident into the photo-diode, so that the sensing accuracy may be reduced.

In contrast, the wearable photoluminescence sensor according to the second aspect of the present disclosure is designed such that the translucent photo-diode may absorb light on both opposing faces thereof. Thus, light of the first wavelength band may be prevented from being incident into the translucent photo-diode, such that generation of noise due to crosstalk may be prevented.

Further, in the wearable photoluminescence sensor according to the first aspect of the present disclosure as described above, the photo-diode detects light incident only onto one face thereof, such that the photo-diode may not detect an entirety of the light of the second wavelength band emitted in random directions from the sensing film.

On the other hand, when comparing the wearable photoluminescence sensor according to the second aspect of the present disclosure with the wearable photoluminescence sensor according to the first aspect, the wearable photoluminescence sensor according to the second aspect has a structure that the reflective support and the transflective filter are respectively disposed above and below the translucent photo-diode. Thus, the light of the second wavelength band having the photo-luminescence characteristic that has otherwise been lost or transmitted may be re-reflected and thus may be utilized to the maximum so that sensitivity and accuracy of the wearable photoluminescence sensor of the second aspect may be improved.

This second aspect will be described in more detail below with reference to the accompanying drawings.

Figure 5:
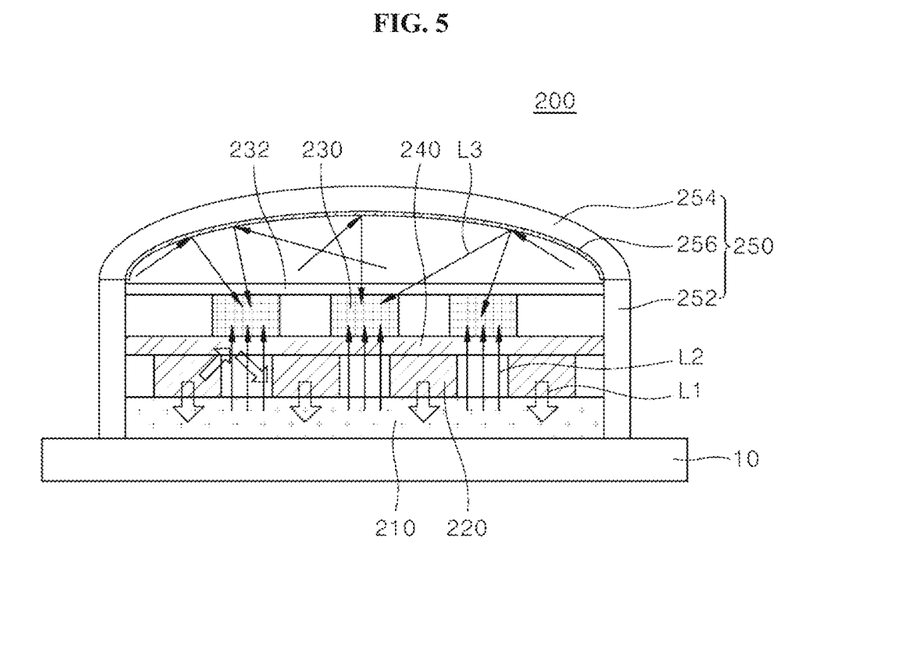
FIG. 5 is a combined cross-sectional view showing a wearable photoluminescence sensor according to a second aspect of the present disclosure.
Figure 6:
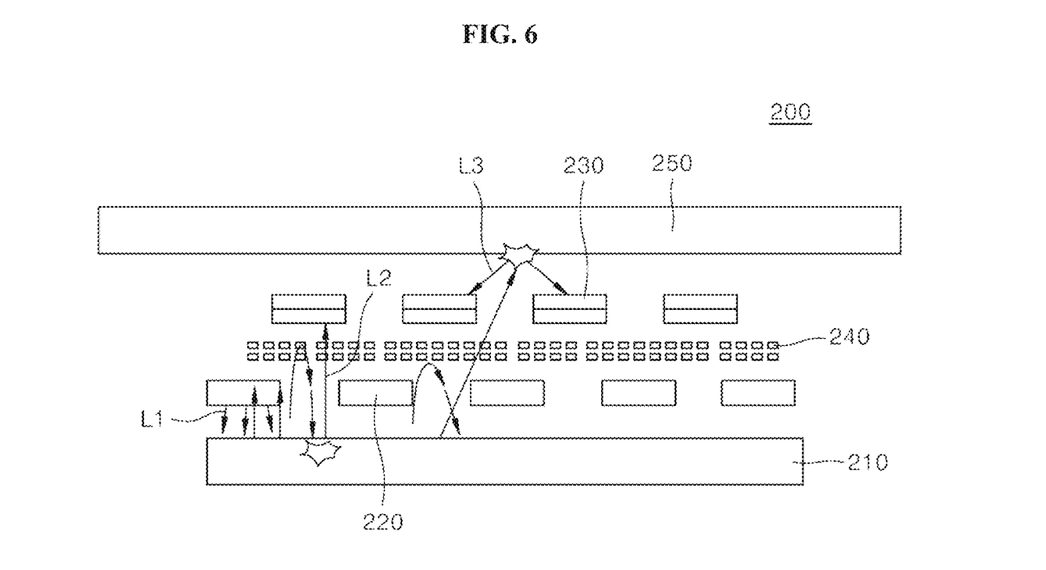
FIG. 6 is a schematic diagram for describing an operating principle of the wearable photoluminescence sensor according to the second aspect of the present disclosure.

FIG. 5 is a cross-sectional view showing a wearable photoluminescence sensor according to the second aspect of the present disclosure. FIG. 6 is a schematic diagram for describing an operating principle of the wearable photoluminescence sensor according to the second aspect of the present disclosure.

Referring to FIG. 5 and FIG. 6, the wearable photoluminescence sensor 200 according to the second aspect of the disclosure includes a sensing film 210, a light-emitting element 220, a translucent photo-diode 230, a transflective filter 240, and a reflective support 250.

The sensing film 210 is attached to the living body as the sensing target. The sensing film 210 may be made of a material capable of sensing oxygen, moisture, nitric oxide, serum, and the like. To this end, the sensing film 210) may contain at least one material selected from a rhodamine-based organic coloring agent including rhodamine 6G, rhodamine 110, rhodamine 700, sulforhodamine B, and sulforhodamine 101, and umbelliferone.

The light-emitting element 220 is disposed on the sensing film 210. The light-emitting element 220 may emit light of a specific wavelength among red, green, and blue wavelength bands. In this connection, the light-emitting element 220 may be an LED (light-emitting diode) or an organic electroluminescence element. Use of the organic electroluminescence element having flexible characteristics may allow the sensor 100 to be easily attached to the living body as a sensing target.

In this connection, the sensing film 210 absorbs light L1 emitted from the light-emitting element 220. Further, the sensing film 210 adsorbs a specific compound or element such as oxygen or active oxygen, moisture, nitric oxide, serum, etc. as an analyte as produced from the skin.

In this connection, the sensing film 110 may absorb light L1 irradiated from the light-emitting element 220, and then may emit light L2 of a specific wavelength having photoluminescence PL characteristic varying based on a type of the specific compound or element toward the photo-diode 230).

That is, when light L1 of the first wavelength band from the light-emitting element 220 is irradiated to the sensing film 210, the sensing film 210 absorbs the light of the first wavelength band, and then emits light L2 of the second wavelength band which becomes larger than the first wavelength band due to the photoluminescence varying based on the content of the specific compound or element.

The translucent photo-diode 230 is disposed above and is spaced from the light-emitting element 220 and at least partially and vertically non-overlaps the light-emitting element. This translucent photodiode 230 detects light L2 emitted from the sensing film 210, and measures an amount of light including information about a content of oxygen ($O_2$) or active oxygen, moisture, nitric oxide, or serum and generates photocurrent based on the measured amount. To this end, means for analyzing and calculating the light L2 emitted from the sensing film 110 may be further provided in the sensor 200.

Figure 7:
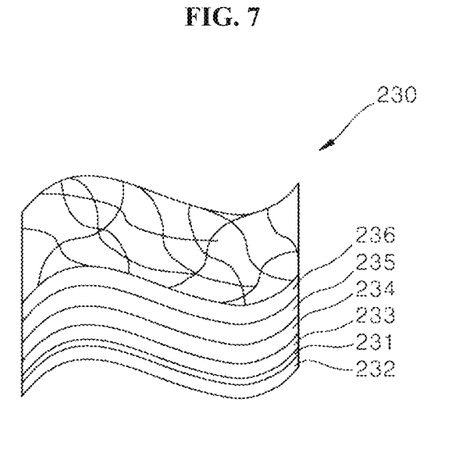
FIG. 7 is a perspective view showing an example of a translucent photo-diode of FIG. 5.
Figure 8:
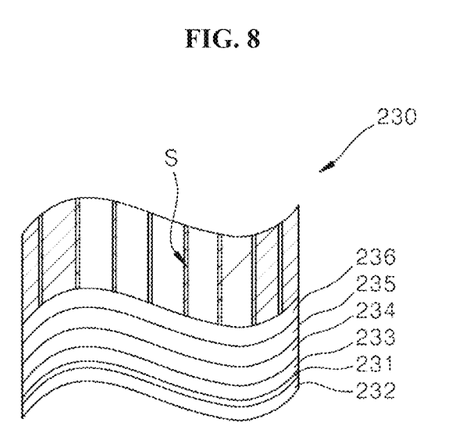
FIG. 8 is a perspective view showing another example of the translucent photo-diode of FIG. 5.

In this connection, FIG. 7 is a perspective view showing an example of the translucent photo-diode of FIG. 5. FIG. 8 is a perspective view showing another example of the translucent photo-diode in FIG. 5. Referring to FIG. 7 and FIG. 8, the translucent photo-diode will be described in more detail.

First, as shown in FIG. 7, the translucent photo-diode 230 may include an insulating substrate 232, a transparent electrode 231, a hole transport layer 233, an active layer 234, an electron transport layer 235, and a translucent electrode 236.

The insulating substrate 232 may be a transparent glass or a transparent polymer film.

The transparent electrode 231 may be made of a transparent conductive metal oxide such as indium tin oxide (ITO), fluorine tin oxide (FTO), indium zinc oxide (IZO). However, the present disclosure is not limited thereto. The transparent electrode 231 is disposed on the insulating substrate 232.

The hole transport layer 233 is disposed on the transparent electrode 231 and provides a path along which holes smoothly move. The hole transport layer 233 may be made of at least one selected from poly(3,4-ethylenedioxy thiophene):poly(styrene sulfonate) (PEDOT:PSS), polyacetylene, polypyrrole, polythiophene, poly(p-phenylenevinylene), etc.

The active layer 234 is disposed on the hole transport layer 233. The active layer 234 may be made of a mixture of a P-type polymer such as a polymer commonly referred to as "P3HT" such as poly(3-hexylthiophene) or poly(3-hexylthiophene-2,5-diyl) and a N-type polymer such as a polymer commonly referred to as 'PCBM' such as methyl [6,6]-phenyl-C61-butanoate onto which a polymer is grafted.

The electron transport layer 235 is disposed on the active layer 234 to provide a path along which electrons smoothly move. The electron transport layer 235 may be made of at least one selected from titanium oxide ($TiO_x$), tungsten oxide ($WO_x$), zinc oxide ($ZnO_x$), iron oxide ($FeO_x$), copper oxide ($CuO_x$), zirconium oxide ($ZrO_x$), chromium oxide ($CrO_x$), vanadium oxide ($Vo_x$), manganese oxide ($MnO_x$), cobalt oxide ($CoO_x$), nickel oxide ($NiO_x$), tin oxide ($SnO_x$), iridium oxide ($IrO_x$), and the like.

In this connection, the holes injected from the hole transport layer 233 and the electrons injected from the electron transport layer 235 react with each other in the active layer 234. Thus, excitons, that is, electron-hole pairs are generated, and then the electrons and holes are separated from each other to generate a photocurrent.

The translucent electrode 236 is disposed on the electron transport layer 235. This translucent electrode 236 may be formed by coating a silver nanowire (AgNWs) solution to a thin thickness of 50 to 150 nm using spraying or spin coating and then drying the coated solution. The silver nanowire AgNWs has high electrical conductivity. Thus, even when the translucent electrode 236 is formed to have a thinness of 50 to 150 nm, there is no problem in securing electrical conductivity, and thus the translucent electrode 236 may have high transmittance characteristic.

Accordingly, the translucent photo-diode 230 has the transparent electrode 231 and the translucent electrode 236 as both opposing electrodes on both opposing faces thereof, respectively. The translucent characteristic thereof may be secured. Further, each of all of the layers of the translucent photo-diode 230 may be formed using liquid phase deposition, thereby simplifying a manufacturing process.

In one example, the translucent photo-diode 230 according to another example of the present disclosure is substantially the same as the translucent photo-diode shown and described in FIG. 7, except for the translucent electrode 236. Thus, duplicate descriptions thereof should be omitted and following descriptions focus on differences therebetween.

As shown in FIG. 8, the translucent electrode 236 may be made of a metal material having a plurality of slits S defined and arranged at a regular spacing.

In this connection, the translucent electrode 236 has a grid structure having the regular spacing of 1 mm to 3 mm. Each of the plurality of slits S has a width of 0.1 mm to 0.3 mm. Accordingly, since light may pass through the plurality of slits S, each having a width of 0.1 mm to 0.3 mm, the translucent characteristic may be secured.

The translucent electrode 236 may be formed by depositing at least one selected from aluminum (Al), gold (Au), silver (Ag), platinum (Pt), palladium (Pd), copper (Cu), tungsten (W), iron (Fe), nickel (Ni), zinc (Zn), etc. on the electron transport layer 235 to form a metal layer, and then selectively etching the metal layer.

In one example, referring back to FIG. 5 and FIG. 6, the transflective filter 240 is disposed between the light-emitting element 220 and the translucent photo-diode 230. Accordingly, the light-emitting element 220 is disposed on the sensing film 210, and the translucent photo-diode 230 is disposed on the transflective filter 240. As a result, the light-emitting elements 220 and the translucent photo-diodes 230 may constitute different layers, respectively and may be arranged alternately with each other.

In this connection, the translucent photo-diode 230 disposed on the transflective filter 240 may only partially overlap with the light-emitting element 220, or may not overlap with the light-emitting element 220.

This transflective filter 240 selectively transmits only the light L2 of the second wavelength band emitted from the sensing film 210. To this end, the transflective filter 240 may include a bandpass filter that transmits light of a specific wavelength band, and absorbs and/or reflects light of a remaining wavelength band.

Accordingly, the transflective filter 240 may selectively filter light L1 of the first wavelength band as emitted from the light-emitting element 220 to minimize an interference effect due to noises flowing into the translucent photo-diode 230, and may selectively allow light L2 of the second wavelength band generated from the sensing film 210 to pass therethrough. In one example, the first wavelength band may be 500 nm to 600 nm, and the second wavelength band may be 601 to 700 nm. However, the disclosure is not limited thereto.

The reflective support 250 is disposed above and spaced from the translucent photo-diode 230.

The reflective support 250 includes a first support frame 252, a second support frame 254 and a reflective layer 256.

The first support frame 252 may extend in a vertical direction. The first support frame 252 may be attached to side walls of the sensing film 210, the light-emitting element 210, and the transflective filter 240).

The second support frame 254 is connected to the first support frame 252 and covers a top of the translucent photo-diode 230. The second support frame 254 may have a semicircular shape when viewed in a cross-sectional view. However, this is merely exemplary and various shapes may be applied thereto. In this connection, the second support frame 254 may be spaced apart from the translucent photo-diode 230 by a predetermined spacing.

Each of the first and second support frames 252 and 254 may be made of at least one material selected from polyimide (PI), polyethylene terephthalate (PET), polydimethylsiloxane (PDMS), polymethyl methacrylate (PMMA), poly(N,N-dimethylacrylamide) (PDMA), polypropylene (PP), polyamide imide, polycarbonate (PC), polyarylate, polyetherimide, polyethylenenaphthalate, and polyphthalamide.

The reflective layer 256 is disposed on the second support frame 254 and re-reflects the light L2 emitted from the sensing film 210 back to the translucent photo-diode 230. In other words, the reflective layer 256 re-reflects the light L2 of the second wavelength band emitted from the sensing film 210 and not incident into the translucent photo-diode 230 but passing through the translucent photo-diode 230 toward the translucent photo-diode 230 such that the re-reflected light L3 is incident into the translucent photo-diode 230.

For this purpose, the reflective layer 256 may be made of a metallic material having a reflectance of the light L2 of the second wavelength band that is approximately twice or higher than the reflectance of the light L1 of the first wavelength band emitted from the light-emitting element 220. Therefore, the reflective layer 256 may be made of at least one selected from Au, Cu, Ag, Al, Pd, Pt, Ru and Rh. The reflective layer 256 may be formed by depositing the above-described metal material on the entire surface of the second support frame 254 or only on a face thereof facing toward the translucent photo-diode 230 using a sputtering scheme.

In this connection, the light L2 of the second wavelength band having a photo-luminescence characteristic as emitted from the sensing film 210 is emitted in random directions. In this connection, a portion of the light L2 emitted from the sensing film 210 not being absorbed into the translucent photo-diode 230 but bypassing the diode 230 may re-reflected from the reflective layer 256 of the reflective support 250 covering the top of the translucent photo-diode 230 and then may be re-absorbed into the diode 230.

Accordingly, the wearable photoluminescence sensor 200 according to the second aspect of the present disclosure minimizes the loss of the light L2 of the second wavelength band having a photo-luminescence characteristic as emitted from the sensing film 210 and introduced into the translucent photo-diode 230, such that the sensing accuracy and sensitivity may be improved.

The wearable photoluminescence sensor 200 according to the second aspect of the present disclosure as described above may have the translucent photo-diode 230, and have a structure in which the transflective filter 240 is disposed between the light-emitting element 220) and the translucent photo-diode 230, and the reflective support 250 is disposed above the translucent photo-diode 230, such that the translucent photo-diode 230 may absorb the light on both opposing faces thereof.

Thus, even when the light-emitting element 220 of the wearable photoluminescence sensor 200 according to the second aspect of the present disclosure is activated using the same power level as that used in the first aspect, the wearable photoluminescence sensor 200 according to the second aspect of the present disclosure may detect the light of the second wavelength band in a more reliable manner than in the first aspect. Thus, the sensitivity of the wearable photoluminescence sensor 200 according to the second aspect of the present disclosure may be further improved.

Further, the wearable photoluminescence sensor 200 according to the second aspect has a structure that the reflective support 250 and the transflective filter 240 are respectively disposed above and below the translucent photo-diode 230. Thus, the light L2 of the second wavelength band having the photo-luminescence characteristic that has otherwise been lost or transmitted may be re-reflected and thus may be utilized to the maximum so that sensitivity and accuracy of the wearable photoluminescence sensor 200 of the second aspect may be improved, compared to the wearable photoluminescence sensor 100 of the first aspect.

In particular, the transflective filter 240 according to the present disclosure may selectively reflect the light L1 of the first wavelength band emitted from the light-emitting element 220 to minimize the interference effect due to noises otherwise flowing into the translucent photo-diode 230, and may selectively allow the light L2 of the second wavelength band emitted from the sensing film 210 to pass therethrough.

As a result, the wearable photoluminescence sensor 200 according to the second aspect of the present disclosure may minimize loss of the light L2 of the second wavelength band having the photo-luminescence characteristic as emitted from the sensing film 210 and flowing into the translucent photo-diode 230, such that sensing accuracy and sensitivity thereof may be improved.

Figure 9:
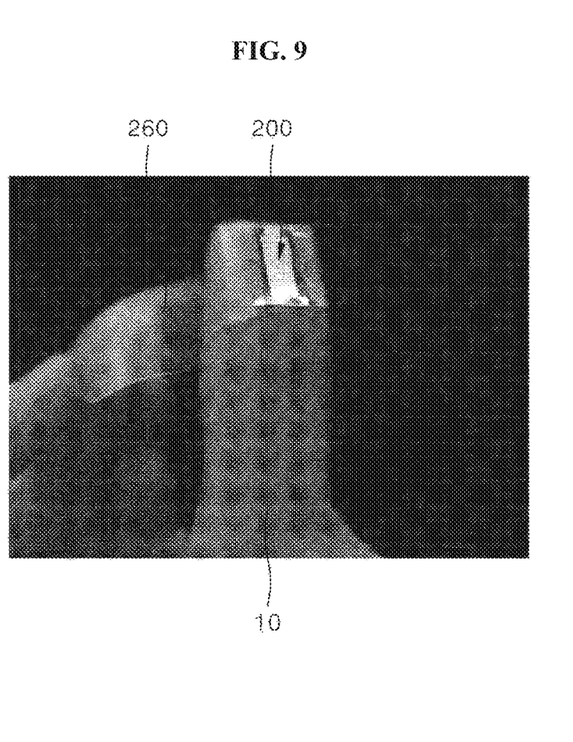
FIG. 9 is a photograph showing a state in which the wearable photoluminescence sensor according to the second aspect of the present disclosure is attached to a skin of a human body using an adhesive member.
Figure 10:
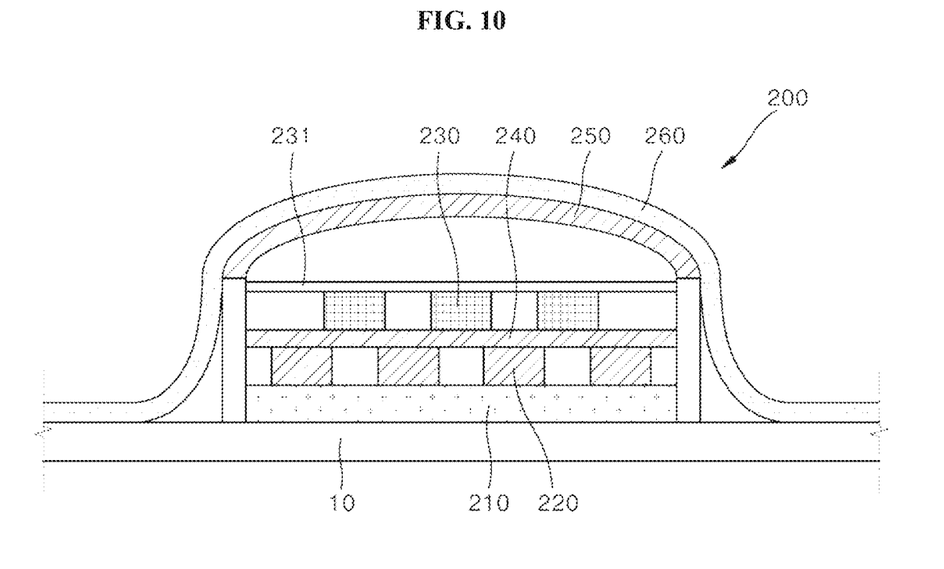
FIG. 10 is a schematic diagram showing a state in which the wearable photoluminescence sensor according to the second aspect of the present disclosure is attached to the skin of the human body using an adhesive member.

In one example, FIG. 9 is a photograph showing a state in which the wearable photoluminescence sensor according to the second aspect of the present disclosure is attached to the skin of the human body using an adhesive member. FIG. 10 is a schematic diagram showing a state in which the wearable photoluminescence sensor according to the second aspect of the present disclosure is attached to the skin of the human body using an adhesive member.

As shown in FIG. 9 and FIG. 10, the wearable photoluminescence sensor 200 according to the second aspect of the present disclosure may be attached to and detached from the skin of the human body 10, specifically, a finger of the human body 10 via an adhesive member 260. In this connection, any material for the adhesive member 260 may be used without particular limitation as long as the material has adhesive ability and flexibility and elasticity and biocompatibility.

In one example, when operating the wearable photoluminescence sensor 200 according to the second aspect of the present disclosure in a state in which the sensor 200 is attached to the finger 10 of a person having a disease such as diabetes via the adhesive member 260, the oxygen concentration in the finger may be detected in real time based on the change in the light intensity characteristic of the photoluminescence PL as emitted from the sensing film 210.

In this connection, the wearable photoluminescence sensor 200 according to the second aspect of the present disclosure wirelessly transmits the measured oxygen concentration to a remote location such as a medical facility, so that a specialist may check the health status of the user 10 in real time.

Accordingly, the wearable photoluminescence sensor 200 according to the second aspect of the present disclosure detects the biological state of the user 10 in real time, and wirelessly transmits the detected state to a remote location such as a medical facility, such that a specialist may easily check the health status of the user 10.

As a result, the wearable photoluminescence sensor 200 according to the second aspect of the present disclosure detects the biological state of the user 10 in real time such that the medical staff may easily check the health state of the user 10, thereby conducting early diagnosis of diseases in real time even at a remote location.

This remote check and diagnosis will be described in more detail below with reference to the accompanying drawings.

Figure 11:
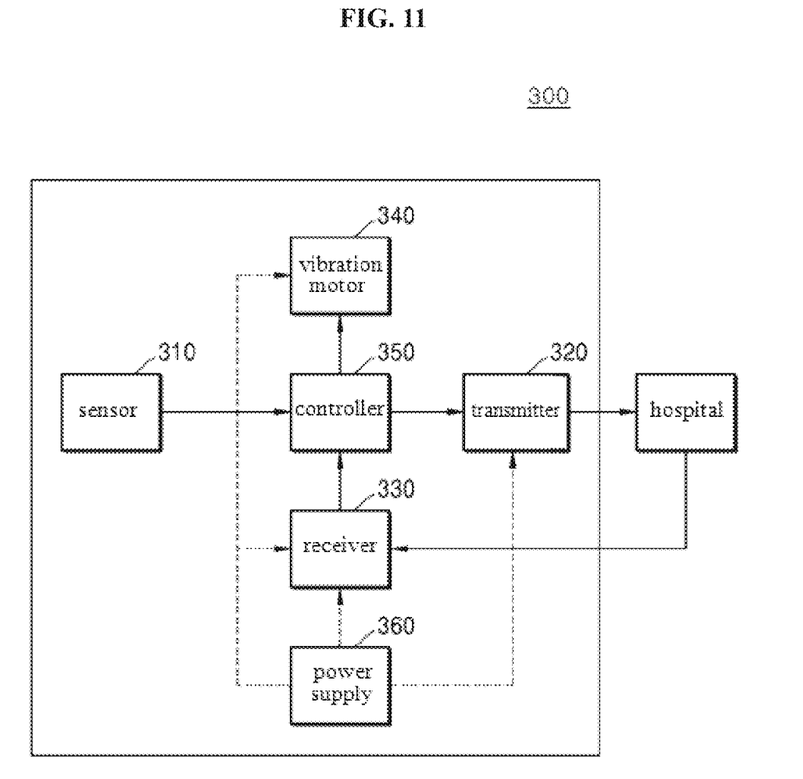
FIG. 11 is a block diagram showing a wearable remote sensing device according to a third aspect of the present disclosure.

FIG. 11 is a block diagram showing a wearable remote sensing device according to a third aspect of the present disclosure.

Referring to FIG. 11, a wearable remote sensing device 300 according to the third aspect of the present disclosure may include a sensor 310, a transmitter 320, a receiver 330, a vibration motor 340, a controller 350, and a power supply 360.

The sensor 310 may include each of the wearable photoluminescence sensors (100 in FIGS. 1 and 200 in FIG. 5) according to the first and second aspects of the present disclosure 100. The wearable photoluminescence sensor 200 may be used according to the second aspect of the present disclosure.

In particular, the biological information measured by the sensor 310 is transmitted to the controller 350. The controller 350 controls the transmitter 320 to wirelessly transmit the information to a remote medical center such as a hospital.

When the specialist who received and analyzed the biological information at the remote medical center determines that a current sender (patient) is in an abnormal state, he/she wirelessly transmits an alarm to suggest that the patient visits the hospital. Accordingly, the alarm is wirelessly received by the receiver 330 which in turn sends the alarm to the controller 350. The controller 350 activates a vibration motor 340 based on the alarm to notify the patient of the hospital visit request.

In one example, the wearable remote sensing device 300 according to the third aspect of the present disclosure may further include the power supply 360. This power supply 360 may be a small DC supply device such as a battery. The controller 350 may check a remaining power amount of the power supply 360. When the power amount is lower than a preset amount, the controller 350 activates the vibration motor 340 to notify the patient of the insufficient power amount.

Therefore, the wearable remote sensing device 300 according to the third aspect of the present disclosure detects the biological state of the user in real time using the sensor 310, and then wirelessly transmits the information to a remote location such as a hospital, thereby allowing the specialist to monitor the health state of the user.

In the above description, the present disclosure has been mainly described based on the aspects. However, various changes or modifications may be made thereto at a level of a person skilled in the art. Therefore, it will be understood that such changes and transformations fall within the scope of the present disclosure as long as they do not depart from the scope of the present disclosure.

What is claimed is:

1. A wearable photoluminescence sensor comprising:
   a light-emitting element emitting a first light of a first wavelength band;
   a sensing film emitting a second light of a second wavelength band different from the first light after absorbing the first light, wherein the sensing film is disposed below the light-emitting element;
   a translucent photo-diode disposed above and spaced apart from the light-emitting element and at least partially and vertically non-overlapping with the light-emitting element, wherein the translucent photo-diode includes a first side and a second side opposite to the first side;
   a transflective filter disposed between the light-emitting element and the first side of the translucent photo-diode; and
   a reflective support disposed above and spaced apart from the translucent photo-diode, the reflective support includes a reflective layer facing the second side of the translucent photo-diode,
   wherein the reflective layer reflects the second light of the second wavelength band to the second side of the translucent photo-diode, and
   wherein the second light of the second wavelength band is absorbed from each of the first side and the second side of the translucent photo-diode.

2. The wearable photoluminescence sensor of claim 1, wherein the light-emitting element includes a light emitting diode (LED) or an organic electroluminescence element emitting light in one of red, green, and blue wavelength bands.

3. The wearable photoluminescence sensor of claim 1, wherein the sensing film contains at least one of a rhodamine-based organic coloring agent including rhodamine 6G, rhodamine 110, rhodamine 700, sulforhodamine B, and sulforhodamine 101, and umbelliferone.

4. The wearable photoluminescence sensor of claim 1, wherein the reflective support includes:
   a first support frame extending in a vertical direction; and
   a second support frame connected to the first support frame and covering a top of the translucent photo-diode, wherein the second support frame includes the reflective layer.

5. The wearable photoluminescence sensor of claim 4, wherein each of the first and second support frames is made of at least one of polyimide (PI), polyethylene terephthalate (PET), polydimethylsiloxane (PDMS), polymethyl methacrylate (PMMA), poly(N,N-dimethylacrylamide) (PDMA), polypropylene (PP), polyamide imide, polycarbonate (PC), polyarylate, polyetherimide, polyethylenenaphthalate, and polyphthalamide.

6. The wearable photoluminescence sensor of claim 4, wherein the reflective layer is made of at least one of Au, Cu, Ag, Al, Pd, Pt, Ru and Rh.

7. The wearable photoluminescence sensor of claim 1, wherein the transflective filter allows only the second light of the second wavelength band emitted from the sensing film to selectively pass therethrough.

8. The wearable photoluminescence sensor of claim 7, wherein the transflective filter includes a bandpass filter.

9. The wearable photoluminescence sensor of claim 1, wherein the translucent photo-diode includes:
   an insulating substrate;
   a transparent electrode disposed on the substrate;
   a hole transport layer disposed on the transparent electrode;

a light absorbing layer disposed on the hole transport layer;

an electron transport layer disposed on the light absorbing layer; and a translucent electrode disposed on the electron transport layer.

10. The wearable photoluminescence sensor of claim 9, wherein the translucent electrode includes a nanowire having a thickness of 50 to 150 nm.

11. The wearable photoluminescence sensor of claim 10, wherein the translucent electrode includes a metal material having a plurality of slits defined therein and arranged by a regular spacing.

12. A wearable remote sensing device comprising:

a sensor configured to be attached to a living body to measure a biological state thereof;

a transmitter for wirelessly transmitting the biological state measured by the sensor to a remote location;

a receiver for wirelessly receiving an alarm from the remote location;

a power supply for supplying power to each of the sensor, the transmitter, and the receiver; and a controller configured to transmit information measured by the sensor to the transmitter, and to inform a user of the alarm received by the receiver and information on a power amount of the power supply, wherein the sensor includes:

a light-emitting element emitting a first light of a first wavelength band;

a sensing film emitting a second light of a second wavelength band different from the first light after absorbing the first light, wherein the sensing film is disposed below the light-emitting element;

a translucent photo-diode disposed above and spaced apart from the light-emitting element and at least partially and vertically non-overlapping with the light-emitting element, wherein the translucent photo-diode includes a first side and a second side opposite to the first side;

a transflective filter disposed between the light-emitting element and the first side of the translucent photo-diode; and a reflective support disposed above and spaced apart from the translucent photo-diode, wherein the reflective support includes a reflective layer facing the second side of the translucent photo-diode, wherein the reflective layer reflects the second light of the second wavelength band to the second side of the translucent photo-diode, and wherein the second light of the second wavelength band is absorbed from each of the first side and the second side of the translucent photo-diode.

13. The device of claim 12, wherein the device further comprises a vibration motor for generating the alarm.

14. The device of claim 12, wherein the transflective filter allows only the second light of the second wavelength band emitted from the sensing film to selectively pass therethrough.

15. The device of claim 14, wherein the transflective filter includes a bandpass filter.

\* \* \* \* \*